United States Patent
Giori

[11] Patent Number: 6,143,383
[45] Date of Patent: Nov. 7, 2000

[54] MULTILAYER CHLORINE-FREE FILM WITH BARRIER LAYER OF A POLYAMIDE BLEND AND OSTOMY POUCHES FORMED THEREFROM

[75] Inventor: Claudio Giori, Riverwood, Ill.

[73] Assignee: Hollister Incorporated, Libertyville, Ill.

[21] Appl. No.: 09/083,801

[22] Filed: May 22, 1998

[51] Int. Cl.[7] .............................. A61F 5/44; B65D 30/02; B65D 30/26; B32D 27/32; B32D 27/34

[52] U.S. Cl. .................. 428/35.2; 428/36.7; 428/220; 428/475.8; 428/476.3; 428/520; 428/349; 604/332

[58] Field of Search .................. 428/35.2, 35.7, 428/36.7, 220, 347, 200, 474.4, 475.8, 476.1, 476.3, 476.6, 476.9, 520, 522, 523, 349; 604/332, 334, 333, 335, 342, 343, 344

[56] References Cited

U.S. PATENT DOCUMENTS

| | | | |
|---|---|---|---|
| 4,801,649 | 1/1989 | Statz | 525/183 |
| 4,977,216 | 12/1990 | Elia | 525/183 |
| 5,407,713 | 4/1995 | Wilfong et al. | 428/34.1 |
| 5,496,295 | 3/1996 | Wilfong et al. | 604/332 |
| 5,567,489 | 10/1996 | Allen et al. | 428/34.1 |
| 5,643,375 | 7/1997 | Wilfong et al. | 156/244.24 |
| 5,895,694 | 4/1999 | Zavadsky et al. | 428/36.7 |

FOREIGN PATENT DOCUMENTS

| | | |
|---|---|---|
| 58-029854A | 2/1983 | Japan . |
| 6009833A | 1/1994 | Japan . |

OTHER PUBLICATIONS

Derwent Abstract of JP 6–9833A; Showa; Resin Composition With High Compatability and Gas Barrier Properties, 1994.

Derwent Abstract of JP 58–29854A; Toray; Flexible Shock Resistant Polyamide Resin Composition, 1983.

*Primary Examiner*—Ellis Robinson
*Assistant Examiner*—John J. Figueroa
*Attorney, Agent, or Firm*—Tilton Fallon Lungmus

[57] ABSTRACT

A multilayer heat-sealable chlorine-free film of relatively low modulus, high interlaminar strength, and low noise upon flexing is provided. The film includes an odor barrier layer and at least one directly adjoining heat-sealable skin layer. The barrier layer is composed of either an aliphatic or partially aromatic polyamide resin, or a blend thereof, blended with an ionomer resin consisting essentially of a partially neutralized ethylene-methacrylic acid copolymer, and the heat-sealable skin layer or layers bonded directly to the barrier layer are composed of copolymers of ethylene and an ester-containing comonomer. High resistance to delamination of the barrier layer and skin layer(s) is achieved without tie layers therebetween. Pouches formed of such multilayer chlorine-free films are also disclosed.

15 Claims, 1 Drawing Sheet

MULTILAYER CHLORINE-FREE FILM WITH BARRIER LAYER OF A POLYAMIDE BLEND AND OSTOMY POUCHES FORMED THEREFROM

BACKGROUND AND SUMMARY

Films for ostomy applications should have good odor barrier properties and produce minimal noise when flexed or wrinked to avoid embarrassment to users. Typically, films currently in use for ostomy applications utilize polyvinylidene chloride (PVDC) or copolymers of vinylidene chloride with a comonomer such as methylacrylate or vinylchloride as the gas barrier layer of a multilayer film. Such multilayer films have good resistance to odor transmission and are also relatively quiet; however, they are also believed to be hazardous to the environment when disposed of by incineration, a common practice in numerous countries. Chlorinated polymers generate hydrochloric acid as a byproduct of incineration and are believed to be a significant contributor to hydrochloric acid release from incinerator flue gases. Furthermore, chlorinated polymers are believed to form toxic dioxin derivatives as byproducts of incineration which are retained in the ashes and may possibly cause solid waste disposal problems.

Unfortunately, films formed of chlorine-free barrier resins tend to be stiffer and noisier than films utilizing conventional PVDC-based resins and do not match the quality of conventional chlorinated films for use in ostomy appliances. Thus, a need exists for a multilayer film which is chlorine-free, can be manufactured by coextrusion from readily available raw materials, is heat sealable, has high softness and low noise when flexed or wrinkled, and is impermeable to fecal odors.

U.S. Pat. No. 5,567,489 discloses a multilayer barrier film in which a chlorine-free barrier layer is composed of amorphous nylon, crystalline nylon, copolymers of ethylene and vinyl alcohol, or blends thereof. Although data presented in the patent indicate the multilayer films to be comparable in quietness to some chlorinated films in general commercial use, experience has revealed that such chlorine-free films are nevertheless significantly noisier than the chlorine-containing films commonly employed for the fabrication of ostomy pouches. The general observation is that unmodified nylon resins are high modulus, stiff materials that do not lend themselves to the production of low noise ostomy films. This is true of all nylon (polyamide) barrier resins, both crystalline and amorphous.

A further disadvantage of unmodified nylon resins is that they are generally incompatible with typical resins used for the heat-sealable outer skin layers and necessitate the use of intermediate adhesion-promoting tie layers between a nylon barrier layer and such skin layers. For example, U.S. Pat. No. 5,567,489 discloses the use of tie layers formed of copolymers of ethylene and vinyl acetate, or copolymers of ethylene and acrylic acid, to improve the adhesion between the core and skin layers. The result is a multilayer film having at least five layers, at least in those embodiments in which two outer skin layers are provided.

Other references illustrating the current state of the art relating to chlorine-free multilayer films are U.S. Pat. Nos. 5,496,295, 5,643,375, and 5,407,713.

One aspect of this invention lies in the discovery that if an odor-barrier layer of a chlorine-free multilayer film is composed of a blend of nylon (polyamide) resin with an ionomer resin, instead of straight nylon, stiffness is significantly reduced and film structures can be produced with lower noise than those containing unmodified nylon. Surprisingly, it has been found that the reduction in noise can be achieved with no measurable loss in odor barrier properties. A further advantage of using a nylon-ionomer resin blend is that unlike unmodified nylons which necessitate the use of intermediate adhesion-promoting tie layers between a nylon barrier layer and the outer skin layers, ionomer-modified nylons have good compatibility and provide excellent adhesion to polyacrylate-type skin layer resins, thus allowing the fabrication of multilayer films (with two outer skin layers) of a total of three rather than five layers. It has been found that high interfacial adhesion can be achieved even at low levels of ionomer in the blend.

The nylon barrier layer may be composed of either an aliphatic or a partially aromatic polyamide, or a blend thereof, blended with an ionomer resin consisting essentially of a partially neutralized ethylene-methacrylic acid copolymer. Nylon/ionomer blends ranging from 30 to 90% nylon and 70 to 10% ionomer by weight are believed effective, with the preferred ratios falling in the range of 50 to 70% nylon and 50 to 30% ionomer.

The multilayer chlorine-free film includes at least one heat-sealable skin layer, preferably two such skin layers, coextruded with and directly contacting the blended nylon/ionomer barrier layer. Each skin layer is composed of a copolymer of ethylene and an ester-containing comonomer such as methyl acrylate, ethyl acrylate, butyl acrylate or vinyl acetate. Preferably, the skin layer composition is a resin composed of a copolymer of ethylene and methyl acrylate (EMA) having a methyl acrylate content in the range of about 10 to 30% by weight.

The result is a multilayer heat-sealable chlorine-free film particularly suitable for the fabrication of ostomy pouches and other waste collection pouches because of its effective odor barrier properties, relatively low noise when flexed or wrinkled, low modulus or high softness, and high interlaminar strength even when no tie layers are used. The ionomer content of the modified nylon barrier layer promotes strong resistance to delamination, and the heat sealability of the skin layer or layers assures that the walls of a pouch formed of such multilayer film may be securely welded to each other by heat sealing, including RF sealing. A pouch formed of the multilayer film of this invention therefore has properties comparable to those exhibited by high-quality pouches formed of chlorine-containing compositions but without the environmental shortcomings described above.

Other features, advantages and objects of the invention will become apparent from the specification and drawings.

DRAWINGS

DETAILED DESCRIPTION OF PREFERRED EMBODIMENTS

The multilayer barrier film of the present invention may be produced using standard coextrusion techniques involving either casting or blowing. Preferably, the multilayer film has three layers—a chlorine-free barrier layer sandwiched between two heat-sealable skin layers—but the advantages of the invention may be at least partially achieved in a two-layer structure having a barrier layer and a single skin layer. Also, while the avoidance of tie layers is a significant advantage of this invention, it is to be understood that one or more tie layers, or additional layers for the purpose of achieving other objectives, may be included if desired.

Figure 1:
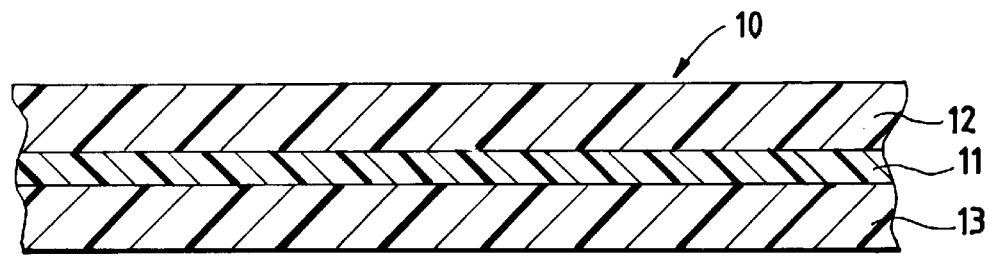
FIG. 1 is a schematic cross-sectional view of an embodiment of the multilayer barrier film of this invention.

FIG. 1 schematically illustrates a multilayer barrier film 10 having a barrier layer 11 sandwiched between skin layers 12 and 13. The chlorine-free barrier layer 11 comprises a blend of nylon (polyamide) resin and an ionomer resin. The nylon component may be crystalline nylon, amorphous nylon, or blends of amorphous and crystalline nylons. Aliphatic nylons such as nylon 6, nylon 66, and nylon 6/66, and partially aromatic nylons, are all believed suitable. Aliphatic nylons are commercially available from several sources such as E.I. duPont deNemours, Allied Signal, and BASF. A partially aromatic nylon is commercially available as Selar PA3426 from E.I. duPont deNemours, Inc., Wilmington, Del.

The ionomer resin blended with the nylon resin consists essentially of a partially neutralized ethylene-methyacrylic acid copolymer. Several ionomers of this type are commercially available from E.I. duPont deNemours under the Surlyn trademark. Surlyn AM7927 and Surlyn AM7928 are preferred because they are already formulated with low levels of nylon and lend themselves to further blending with nylon without precompounding. The nylon/ionomer ratio may vary considerably with nylon constituting 30 to 90% by weight, and the ionomer 70 to 10% by weight, of the blend. Preferably, the percentage of nylon should be in the range of 50 to 70% and that of ionomer in the range of 50 to 30%.

Skin layers 12 and 13 are formed of a copolymer of ethylene and an ester-containing comonomer such as methyl acrylate, ethyl acrylate, butyl acrylate, or vinyl acetate. A particularly effective skin layer composition capable of high interfacial adhesion strength with the barrier layer 11 with which it is coextruded is a resin composed of a copolymer of ethylene and methyl acrylate (EMA) having a methyl acrylate content in the range of about 10 to 30% by weight. Ideally, the methyl acrylate content is in the range of about 18 to 20% of the skin layer composition.

Figure 2:
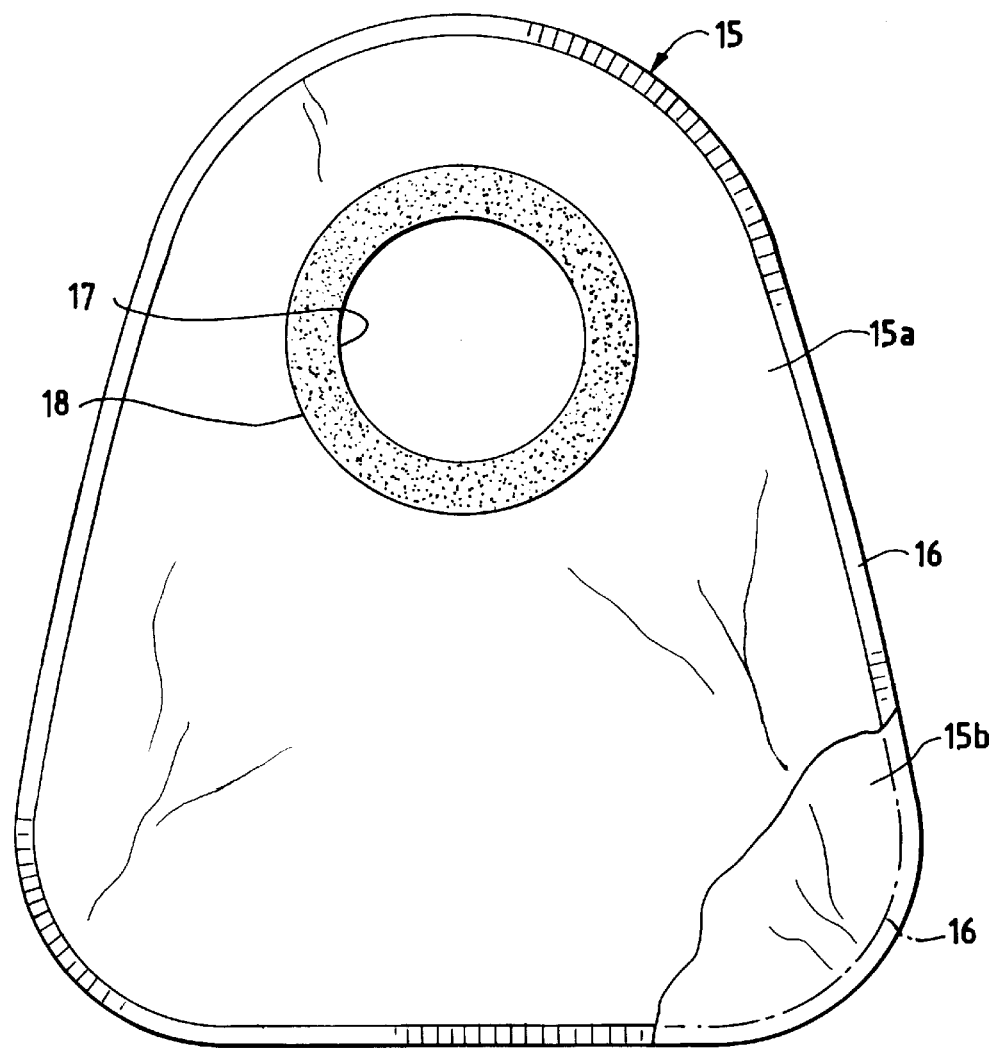
FIG. 2 is an elevational view of an ostomy pouch formed from the multilayer barrier film of FIG. 1.

FIG. 2 illustrates a typical ostomy pouch 15 having its wall 15a and 15b formed from the multilayer barrier film of FIG. 1. The films are arranged with their respective sealable skin layers 12 (or 13) facing each other and heat sealed together along the outer periphery of the pouch as indicated at 16. One wall of the pouch has a stoma-receiving opening 17 formed therein and an adhesive attchment ring 18 is located about the opening for adhesive attachment to the peristomal skin surfaces of a patient. The pouch as shown is of a type generally referred to as a one-piece appliance but, if desired, a mechanical coupling ring may be substituted for adhesive ring 18, with the pouch therefore becoming one component of a two-piece ostomy appliance, all as well known in the art.

In order that the invention may be more readily understood, reference is made to the following examples which are intended to be illustrative of the invention, but are not intended to be limiting in scope.

EXAMPLE 1

A three-layer barrier film was produced in accordance with the present invention and included a core barrier layer and two outer skin layers joined directly to the core layer. The layers were coextruded using conventional film casting techniques at 450° F., resulting in a multilayer film having a total thickness of approximately 4 mil. The core barrier layer was a 40/60 weight ratio blend of nylon 66/6 (Ultramid C-35, BASF Corp.) and an ionomer (Surlyn AM7928, duPont Co.). The thickness of the barrier layer was approximately 0.6 mil. The two outer skin layers comprised ethylene-methyl acrylate copolymer with 20% by weight methyl acrylate content (EMAC SP2242, Chevron Chemical Co.).

For comparison purposes, a control film was produced, having the same total thickness, barrier thickness, and outer skin layer composition. The only difference concerned the composition of the barrier layer of the control film which was 100% nylon 66/6 (Ultramid C-35, BASF Corp.).

The tensile modulus (psi) of the films were measured on an Instron tester (ASTM D882) with the secant modulus at 2% elongation being determined in both machine direction (MD) and transverse direction (TD). The multilayer films in which the core layer was composed of a nylon/ionomer blend averaged secant moduli at 2% elongation of 8350 MD and 8270 TD, whereas the controls with core layers of 100% nylon averaged 10,560 MD and 12,200 TD, revealing the films made in accordance with this invention to be considerably softer than the control films.

The films were tested for quietness by forming a 4 inch by 4 inch sample of each film into a cylinder and mounting it on a test fixture wherein one end of the cylinder was held fixed and the other was rotated around the cylinder axis at an angle of 15°, 70 cycles/minute. Noise emissions produced by the film flexing were analyzed with a sound level meter giving the following results:

TABLE 1

| Sample | dBA | dB, 8 kHz | dB, 8 kHz |
|---|---|---|---|
| EMA/Nylon Blend/EMA | 64 | 43 | 26 |
| EMA/100% Nylon/EMA | 69 | 51 | 42 |

In this table, dBA is a weighted average that takes into account the human perception of noise over the entire frequency range, whereas dB values in the 8 and 16 kHz octave bands are indicative of the noise in the high freqency range and represent the crispness of the noise. The dBA and dB values in the 8 and 16 kHz octave bands therefore reveal that film samples embodying the invention having core layers of blended nylon were considerably quieter than the control samples in which the core layers were 100% nylon.

The samples were tested for odor transmission using British Standard 7127, Part 101, "Method for Determining Odor Transmission of Colostomy and Ileostomy Bag Materials," British Standard Institution, London England, and the odor transmission of all samples, including the controls, was found negligible. However, considerable difference in delamination resistance was determined qualitatively by heat sealing the film samples and visually examining the mode of failure of the seals in 180° pull tests on an Instron tester. Delamination resistance of the control samples was found to be poor (easy separation of film skin from barrier layer), whereas delamination resistance of samples embodying the invention was revealed to be very high (skin and barrier layer impossible to separate). The outstanding performance of the latter is particularly noteworthy because the secure bond between the EMA skin layers and the blended nylon/ionomer core layer was achieved without the need or presence of tie layers.

EXAMPLE 2

A three-layer barrier film in accordance with this invention was produced by coextrusion using conventional film casting techniques at 450° F., resulting in a multilayer film having a total thickness of about 4 mil and a core barrier layer thickness of 0.4 mil. The composition of the barrier layer was a 64/36 weight ratio blend of nylon 66/6 (Ultramid C-35, BASF Corp.) and ionomer resin (Surlyn AM7928, duPont Co.). The two outer skin layers in direct contact with the core barrier layer were formed of ethylene methyl acrylate copolymer with 20% by weight methyl acrylate content (EMAC SP2242, Chevron Chemical Co.).

A control film having the same total thickness (4 mil), the same barrier thickness (0.4 mil) and the same outer skin layer composition was produced for comparison purposes. As in Example 1, the only difference concerned the composition of the barrier layer of the control film which was 100% nylon 66/6 (Ultramid C-35, BASF Corp.).

Using the same procedure described in Example 1, the tensile modulus (psi) of the films was measured with the secant modulus at 2% elongation being determined in both machine direction and transverse direction. The films having a core layer of nylon/ionomer blend had an average 2% secant modulus of 7,000 psi in the machine direction and 6,690 psi in the transverse direction, compared with the controls with core layers of 100% nylon having an average 2% secant modulus of 8,090 psi in the machine direction and 9,350 psi in the transverse direction.

The films were tested for quietness following the procedure of Example 1, giving the following results:

TABLE 2

| Sample | dBA | dB, 8 kHz | dB, 8 kHz |
|---|---|---|---|
| EMA/Nylon Blend/EMA | 67 | 46 | 32 |
| EMA/100% Nylon/EMA | 69 | 51 | 38 |

All samples were tested for odor transmission using British Standard 7127, Part 101, and tranmission was found negligible. Delamination resistance was determined qualitatively by heat sealing the film samples and visually examining the mode of failure of the seals in 180° pull tests on an Instron tester. The heat seal pull test readily promoted delamination of control samples, whereas samples embodying the invention could not be delaminated by the Instron pull test or other mechanical means.

Examples 1 and 2 reveals that multilayer films embodying this invention have a 2% secant modulus of well under 9,000 psi in both machine (MD) and transverse (TD) directions, whereas the values for the control samples were substantially higher. It is well recognized that 2% secant modulus values are a measure of the stiffness, that is, the lower the modulus the greater the softness (or the lower the stiffness) of a film. In addition, the films characterizing this invention are relatively quiet, exhibiting noise levels of less than about 50 dB in the 8 kHz and 16 kHz octave bands when subjected to flexing through a 15° angle at 70 cycles/minute.

While in the foregoing, embodiments of the invention have been disclosed in detail for purposes of illustration, it will be understood by those skilled in the art that many of these details may be varied without departing from the spirit and scope of the invention.

What is claimed is:

1. A multilayer heat-sealable chlorine-free film of relatively low noise, low modulus and high interlaminar strength, consisting of an odor barrier layer and at least one adjoining heat-sealable skin layer in direct contact with said barrier layer; said barrier layer comprising an aliphatic or partially aromatic polyamide resin or a blend thereof, blended with an ionomer resin consisting essentially of a partially neutralized ethylene-methacrylic acid copolymer; and said heat-sealable skin layer comprising a copolymer of ethylene and an ester-containing comonomer free of anhydride and carboxylic acid groups.

2. The multilayer film of claim 1 in which two of said skin layers are disposed on opposite sides of said odor barrier layer to provide said film with a total of three layers.

3. The multilayer film of claim 2 in which said film has a 2% secant modulus of less than about 9,000 psi in both machine and transverse directions.

4. The multilayer film of claim 2 in which said film exhibits a noise of less than about 50 dB in the 8 kHz and 16 kHz octave bands, respectively, when subjected to flexing through a 15° angle at 70 cycles/minute.

5. The multilayer film of claim 2 in which said skin layers consist essentially of a copolymer of ethylene and an ester-containing comonomer selected from the group consisting of methyl acrylate, ethyl acrylate, butyl acrylate, and vinyl acetate.

6. The multilayer film of claim 2 in which said skin layers are composed essentially of a copolymer of ethylene and methyl acrylate having a methyl acrylate content in the range of about 10 to 30% by weight.

7. The multilayer film of claim 1 in which said blend of polyamide resin and ionomer resin comprises from 30 to 90% polyamide resin and 70 to 10% ionomer resin.

8. The multilayer film of claim 1 in which said blend of polyamide resin and ionomer resin comprises from 50 to 70% polyamide resin and 50 to 30% ionomer resin.

9. An ostomy pouch having two side walls each consisting of a multilayer chlorine-free film having an odor barrier layer coextruded with at least adjoining one heat-sealable skin layer in direct contact therewith; said skin layers of said walls facing each other and being heat sealed along peripheral edge portions of said pouch; said barrier layer of each wall comprising an aliphatic or partially aromatic polyamide resin or a blend thereof, blended with an ionomer resin consisting essentially of a partially neutralized ethylene-methacrylic acid copolymer; and said skin layers each comprising a heat-sealable copolymer of ethylene and an ester-containing comonomer free of anhydride and carboxylic acid groups.

10. The ostomy pouch of claim 9 in which the multilayer film of each of said side walls has two of said heat-sealable skin layers disposed on opposite sides of said barrier layer to provide each multilayer film with a total of three layers.

11. The ostomy pouch of claim 10 in which said film of each of said walls has a 2% secant modulus of less than about 9,000 psi in both machine and transverse directions.

12. The ostomy pouch of claim 10 in which said multilayer film of each of said walls exhibits a noise of less than about 50 dB in the 8 kHz and 16 kHz octave bands, respectively, when subjected to flexing through a 15° angle at 70 cycles/minute.

13. The ostomy pouch of claim 10 in which said skin layers consist essentially of a copolymer of ethylene and ester-containing comonomer selected from the group consisting of methyl acrylate, ethyl acrylate, butyl acrylate, and vinyl acetate.

14. The ostomy pouch of claim 9 in which said blend of polyamide resin and ionomer resin comprises from 30 to 90% polyamide resin and 70 to 10% ionomer resin.

15. The ostomy pouch of claim 9 in which said blend of polyamide resin and ionomer resin comprises from 50 to 70% polyamide resin and 50 to 30% ionomer resin.

* * * * *